United States Patent [19]

Bauer

[11] Patent Number: 5,351,871

[45] Date of Patent: Oct. 4, 1994

[54] INTRANASAL SEPTAL STAPLING DEVICE

[76] Inventor: William Bauer, 80 Summerhill Pl., Newnan, Ga. 30263

[21] Appl. No.: 35,809

[22] Filed: Mar. 23, 1993

Related U.S. Application Data

[63] Continuation-in-part of Ser. No. 858,028, Mar. 26, 1992.

[51] Int. Cl.⁵ ............................................. A61B 17/068
[52] U.S. Cl. .................................. 227/177; 227/175; 227/19
[58] Field of Search ................... 227/19, 175, 176, 177

[56] References Cited

U.S. PATENT DOCUMENTS

| D. 279,501 | 7/1985 | Sprekelmeier et al. | D24/145 |
|---|---|---|---|
| D. 301,740 | 6/1989 | Green | D24/145 |
| 661,598 | 11/1900 | Callison et al. | 72/410 |
| 2,853,074 | 9/1958 | Olson | 227/177 |
| 3,082,426 | 3/1963 | Miles | 606/143 |
| 3,278,107 | 10/1966 | Rygg | 227/143 |
| 3,470,875 | 10/1969 | Johnson | 606/145 |
| 3,575,038 | 4/1971 | Mallett | 72/410 |
| 4,615,474 | 10/1986 | Strekopytov et al. | 227/19 |
| 4,633,861 | 1/1987 | Chow et al. | 227/180 |
| 4,784,137 | 11/1988 | Kulik et al. | 227/19 X |
| 4,991,764 | 2/1991 | Mericle | 227/178 |
| 5,040,715 | 8/1991 | Green et al. | 227/176 |
| 5,125,553 | 6/1992 | Oddsen et al. | 227/175 |

Primary Examiner—Richard K. Seidel
Assistant Examiner—Raymond D. Woods
Attorney, Agent, or Firm—Cushman, Darby & Cushman

[57] ABSTRACT

A stapling device including first and second arms, each arm having a distal portion and a proximal portion; a stapler head rotatably coupled to a free end of the distal portion of the second arm. The stapler head has a first, inoperative position and a second operative position. The device includes a member for moving the stapler head from the inoperative position to the operative position, and elements for pivotably coupling the first arm to the second arm. The stapling device further includes first and second handle elements each pivotably coupled to each other and to the proximal portions of the first and second arms and operatively coupled to the moving member so that initial displacement of the handle elements from an inoperative position towards each other moves the distal portions of the first and second arms towards each other and actuates the moving member to move the stapler head from the inoperative position to the operative position. Further displacement of the handle elements displaces the second arm to bring the stapler head and the first arm into contact with tissue structure to be stapled. Release of the handle elements allows the moving member to return the stapler head to the inoperative position.

13 Claims, 9 Drawing Sheets

INTRANASAL SEPTAL STAPLING DEVICE

This is a Continuation-in-Part of co-pending application Ser. No. 07/858,028 filed Mar. 26, 1992, the disclosure of which is incorporated herein by this reference.

BACKGROUND OF THE INVENTION

1. Field of the Invention

This invention relates to a method and device for applying staple sutures, and more particularly to an intranasal septal stapling device for insertion into the narrow passages of the nose for dispensing staples into septal tissue.

2. Background of the Invention

Septal surgery is among the most common operations performed. It is estimated that 500,000 septal surgeries are performed each year in the United States by Otolaryngologists and Plastic Surgeons.

Septal surgery was first described in 1882, and the techniques have been modified up to the present day to correct the septum and preserve as much cartilage as possible to prevent loss of support and saddling of the external nose. Submucous resection and septoplasty are performed for nasal obstruction, sinusitis, and headache. It is often performed in conjunction with a rhinoplasty for cosmetic results.

Traditional septal surgery begins with an intranasal incision through the lining of the septum. The lining is then elevated away from the supporting skeleton by creating a tunnel on one or both sides of the septum. This allows direct visualization of the distorted bone or cartilage. Repair consists of removing or contouring the bone and cartilage. Support is assured by preserving as much cartilage as possible or by replacing crooked pieces of cartilage with straight pieces. On completion, the septum is conventionally held together with packing or suturing to prevent hematoma formation. However, intranasal packing is generally left in place 24–72 hours and causes great discomfort to the patient. Further, studies have shown that intranasal packing reduces oxygen saturation and can cause toxic shock syndrome. Therefore, intranasal packing is not a benign procedure. Unfortunately, its alternative, intranasal suturing, is technically difficult and sometimes impossible to perform.

SUMMARY OF THE INVENTION

In accordance with the present invention, intranasal stapling is employed as an adjunct to or replacement of intranasal packing following submucous resection of the septum or its variation, septoplasty. Septal stapling is performed so as to support the septal tissues until healing commences. Thus, intranasal septal stapling in accordance with the invention is accomplished by passing a staple through the loose mucosa of the septum and anchoring it to the underlying septal tissue. This may mean simply joining two mucosal surfaces and allowing them to heal together as a single unit. Intranasal septal stapling may also be used in accordance with the invention to hold and secure cartilage or bone between the two mucosal membranes for added support. In the same manner, tissue grafts can be secured to the septum for repair of septal perforations.

Intranasal stapling offers two great advantages. First, the procedure is comfortable for the patient; it prevents complete nasal obstruction, thus reducing the likelihood of headaches and sinus pressure which may occur when intranasal packing is performed. Secondly, for the trained surgeon, intranasal stapling is easily performed and is an extremely quick procedure which saves operating time.

Devices have been developed to apply staple sutures. For example, U.S. Pat. Nos. 3,575,038 and 3,278,107 disclose devices for applying staple sutures to body tissue. These devices, however, are not suitable for intranasal stapling since the stapling arms are too large to pass through the nasal cavity.

More particularly, the depth of the nasal cavity from front to back is about 7 cm in adults. The greatest depth in the nose required for stapling is 5 cm. The width of the septum varies from approximately 1 cm at the columellar entrance to 4 mm throughout the rest of the nose. The distance between the outer walls of the two nasal passages is about 2 cm at the outer nares entrance and 1.3 cm at the pyriform aperture or inner nares. The average width of each nasal passage is about 5 mm.

After a septoplasty the smallest length a staple must have is 5 mm, which allows 3 mm to penetrate the mucosal walls and 2 mm to be crimped. Since a stapler head which drives the staple must be added to the length of the staple, the 5 mm width of the nasal passage will be exceeded. Consequently, conventional stapling devices cannot be utilized for this procedure.

Thus, in accordance with the invention, an intranasal stapling device is provided which can be accommodated by the narrow nasal passages to perform the stapling process and then be easily removed. In accordance with the principles of the present invention, this object is achieved by providing a stapling device including first and second arms, each arm having a distal portion and a proximal portion; a stapler head rotatably coupled to a free end of the distal portion of the second arm. The stapler head has a first, inoperative position and a second operative position. The device includes a member for moving the stapler head from the inoperative position to the operative position, and elements for pivotly coupling the first arm to the second arm. The stapling device further includes first and second handle members each pivotably coupled to each other and to the proximal portions of the first and second arms, with at least one arm being operatively coupled to the moving member so that initial displacement of the handle members from an inoperative position towards each other moves the distal portions of the first and second arms towards each other and actuates the moving member to move the stapler head from the inoperative position to the operative position. Further displacement of the handle members displaces the second arm to bring the stapler head and the first arm into contact with tissue structure to be stapled. Release of the handle members allows the moving member to return the stapler head to the inoperative position.

DETAILED DESCRIPTION OF THE INVENTION

Referring to the drawings, an intranasal septal stapling device, generally indicated at 10, which embodies the principles of the present invention, is shown.

The stapling device 10 includes a stapler arm, generally indicated at 12, an anvil arm, generally indicated at 14, a handle assembly, generally indicated at 16 and a stapler head 18.

Figure 6:
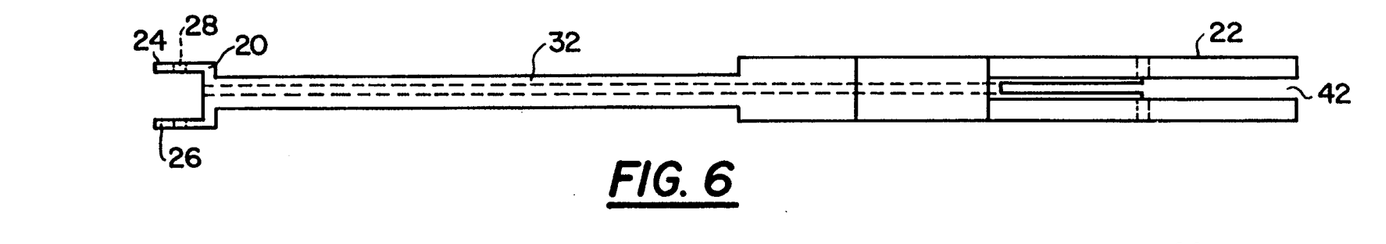
FIG. 6 is plan view of the stapler arm provided in accordance with the principles of the present invention.
Figure 7:
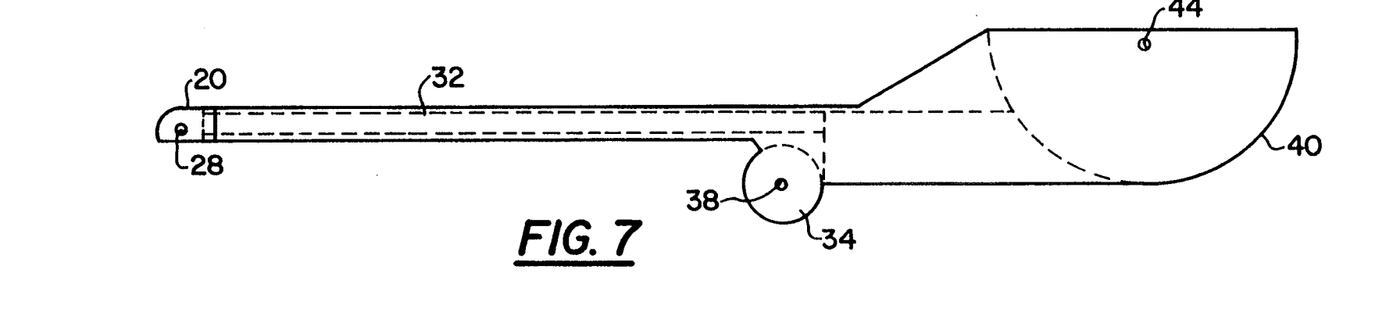
FIG. 7 is a front view of the stapler arm of FIG. 6.
Figure 8:
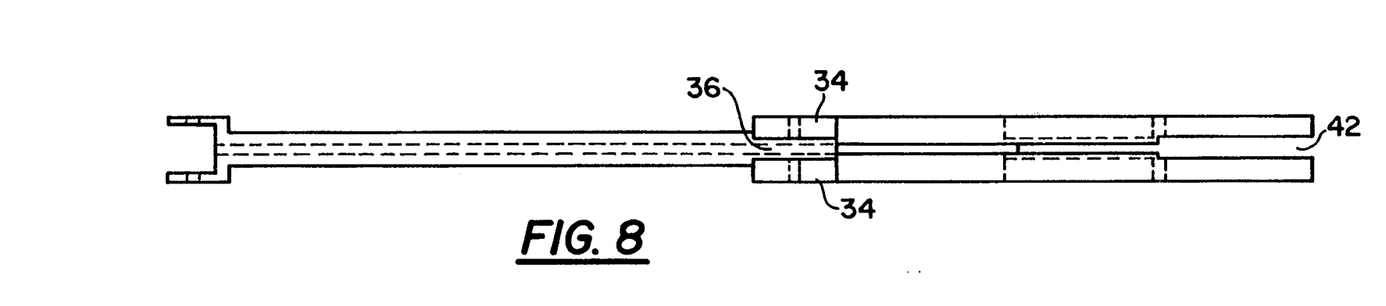
FIG. 8 is a bottom view of the stapler arm of FIG. 6.

The stapler arm 12 has a distal portion 20 and a proximal portion 22, as shown in FIGS. 6-8. The distal portion is of specific length and width so as to be capable of being inserted into a nasal passage and to extend, if necessary, along the length of that passage. The distal portion 20 includes an elongate portion which increases in width upon joining the proximal portion 22 for accommodating the handle assembly, as will become more apparent below. The end of the distal portion includes a forked portion defined by arms 24 and 26, as shown in FIG. 6. Each arm 24, 26 has a bore 28 defined therethrough. The bores 28 have a common longitudinal axis which is perpendicular to the longitudinal axis of the stapler arm. The distal portion 20 has a smoothly curved outer surface (FIG. 7) so to prevent damage to the interior surfaces of the nose when inserted therein. A hollow core 32 extends the length of the distal portion and terminates at the proximal portion 22 of the stapler arm 12.

The proximal portion 22 of the stapler arm 12 includes two leg members 34 which define a channel 36 therebetween. A bore 38 is disposed perpendicular to the longitudinal axis of the stapler arm and extends through each leg member.

End 40 of the proximal portion 22 of the stapler arm has a curved outer periphery and includes a slot 42 disposed along the longitudinal axis of the stapler arm. A bore 44 is defined perpendicular to the longitudinal axis of the stapler arm at end 40. The slot 42 and bore 44 are used to pivotally couple a portion of the handle assembly 16 to the stapler arm.

Figure 16:
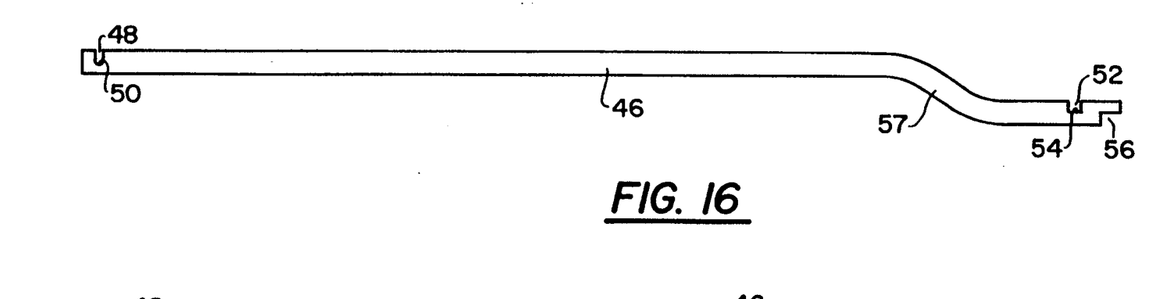
FIG. 16 is a front view of the slide member of the stapler arm provided in accordance with the principles of the present invention.

The stapler arm 12 further includes an elongated slide member 46 (FIGS. 16 and 17) which is slidably disposed in hollow bore 36, which extends along the entire length of the distal portion 20. The distal tip of the slide member 46 includes a slot 48 having a curved surface 50. The slot 48, disposed perpendicular to the longitudinal axis of the slide member, is used to rotatably couple the slide member to the stapler head 18. The proximal end of the slide member also includes a slot 52 having a flat bottom surface 54. A notch 56 is defined at the proximal end of the slide member for coupling to the handle assembly 16, which will become apparent below. The slide member includes a transition portion 57 which places the distal tip in a plane different from a plane in which the proximal end is disposed. The transition portion curves slightly and is constructed from firm, yet resilient material.

Figures 17, 18, 19:
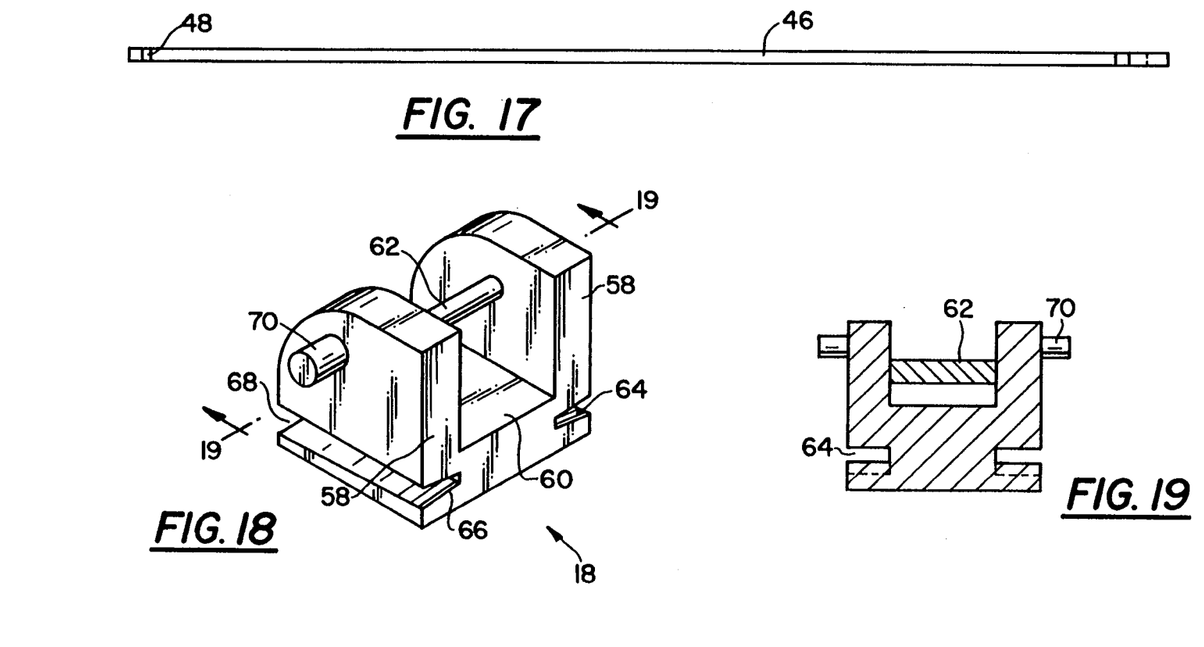
FIG. 17 is a plan view of the slide member of FIG. 16.
FIG. 18 is an enlarged perspective view of the stapler head provided in accordance with the principles of the present invention.
FIG. 19 is a cross-sectional view of the stapler head taken along the line 19—19 of FIG. 18.

The stapling device 10 includes a stapler head 18. As shown in FIGS. 18 and 19, the stapler head 18 includes side members 58 which are joined with base member 60 so as to define a U-shaped member. A rod 62 is disposed between the side members. A portion of the side members have curved outer peripheral surfaces so that no tissue is damaged when the device is inserted into or removed from the nasal passage. A tapered groove 64 is defined in the distal end of each side member 58. The groove tapers so as to gradually widen from end 66 to end 68 for frictionally holding the staple capsule, as will become more apparent below. Side members 58 each have a cylindrical protrusion 70 disposed on an outer surface thereof, about a common axis.

Figure 23:
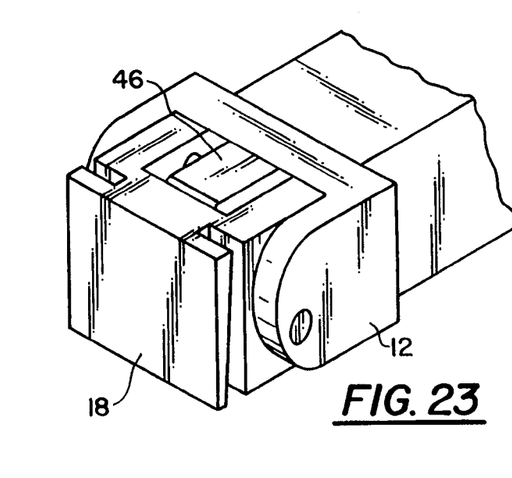
FIG. 23 is a partial perspective view with the stapler head attached and disposed in the operative position.

The rod 62 of the stapler head 18 is coupled with slot 48 of the slide member 46, permitting the stapler head to rotate with respect to the slide member. Protrusions 70 are fitted in bores 28 in the stapler arm 12, so that the stapler head 18 can rotate with respect to the stapler arm. The stapler head is thus fully assembled with the stapler arm, as shown in FIG. 23.

Figure 9:
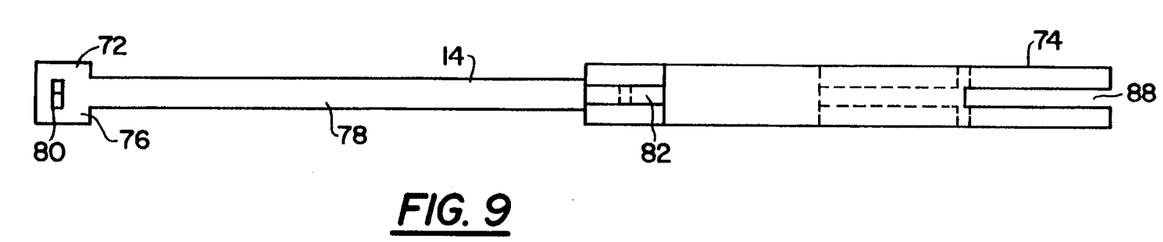
FIG. 9 is a plan view of the anvil arm provided in accordance with the principles of the present invention.
Figure 10:
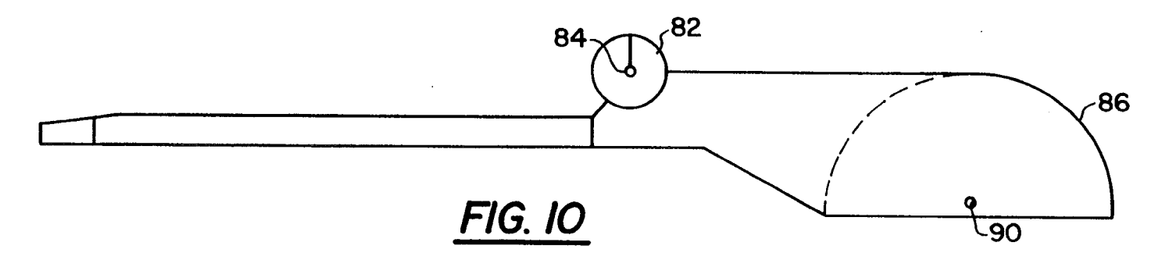
FIG. 10 is a front view of the anvil arm of FIG. 9.
Figure 11:
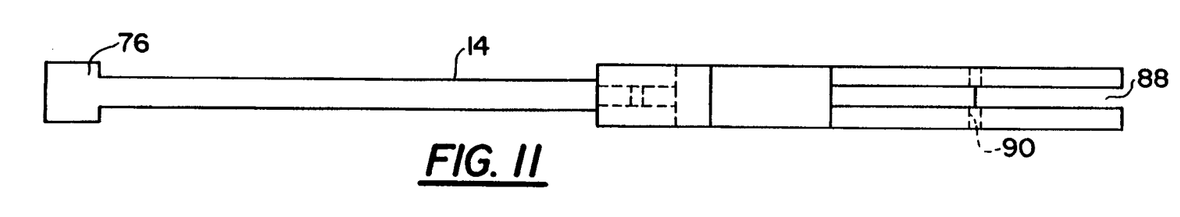
FIG. 11 is a bottom view of the anvil arm of FIG. 9.

The anvil arm 14, as shown in FIGS. 9-11 includes a distal portion 72 and a proximal portion 74. Like the stapler arm, the distal portion 72 is of specific length and width so as to be insertable into and capable of extending along a nasal passage. The distal portion includes an anvil 74 which merges with an elongate portion 78 that terminates at the proximal portion 74. The width of the anvil arm increases at the proximal portion to facilitate coupling to the handle assembly. The angled anvil 74 includes two indentations 80 used bind and close the staple legs during stapling.

The proximal portion 74 of the anvil arm includes a leg 82 protruding therefrom. The leg 82 is sized to fit within channel 36 of the stapler arm. A bore 84 of equal size to bore 38 of the stapler arm, extends through the leg 82, perpendicularly to the longitudinal axis of the anvil arm. A pin 85 (FIG. 2) is disposed through bores 84 and 38 so to pivotally couple the anvil arm to the stapler arm.

End 86 of the proximal portion 72 of the anvil arm has a curved outer periphery. End 86 also includes an slot 88. A bore 90 is disposed at end 86 perpendicular to the longitudinal axis of the anvil arm. The slot 88 and bore 86 are used to pivotally couple the handle assembly 16 to the anvil arm, the function of which will become more apparent below.

Figure 1:
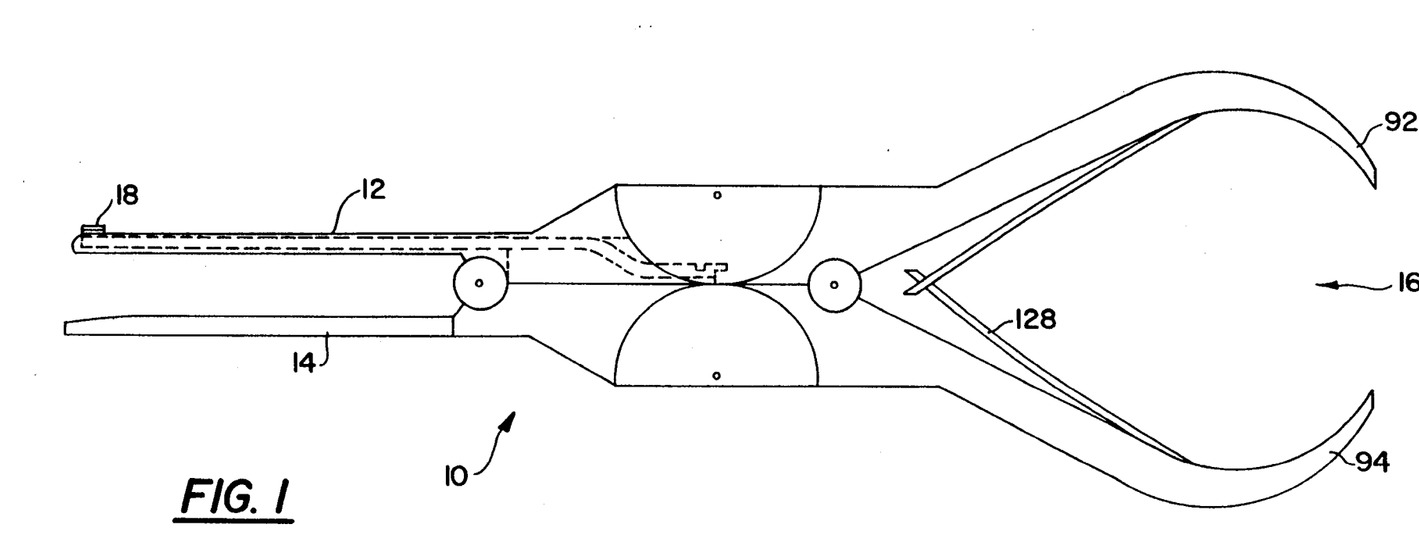
FIG. 1 is a front view, in partial section, of the intranasal septal stapling device embodying the principles of the present invention.
Figure 2:
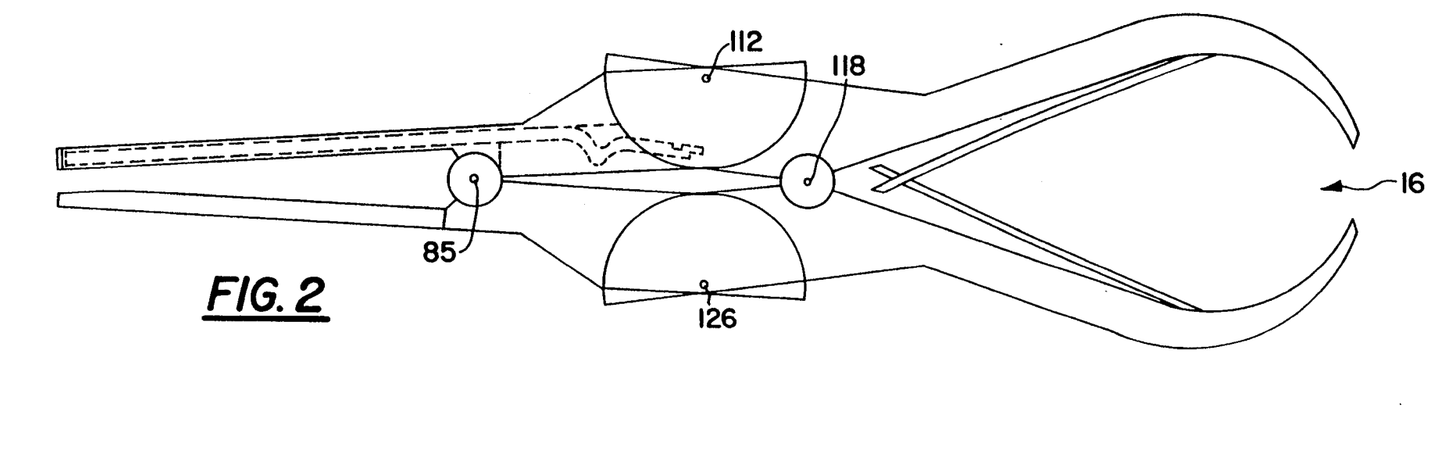
FIG. 2 is front view, in partial section, of the device of FIG. 1 shown with the handles biased toward each other, thus moving the slide member forward.
Figure 3:
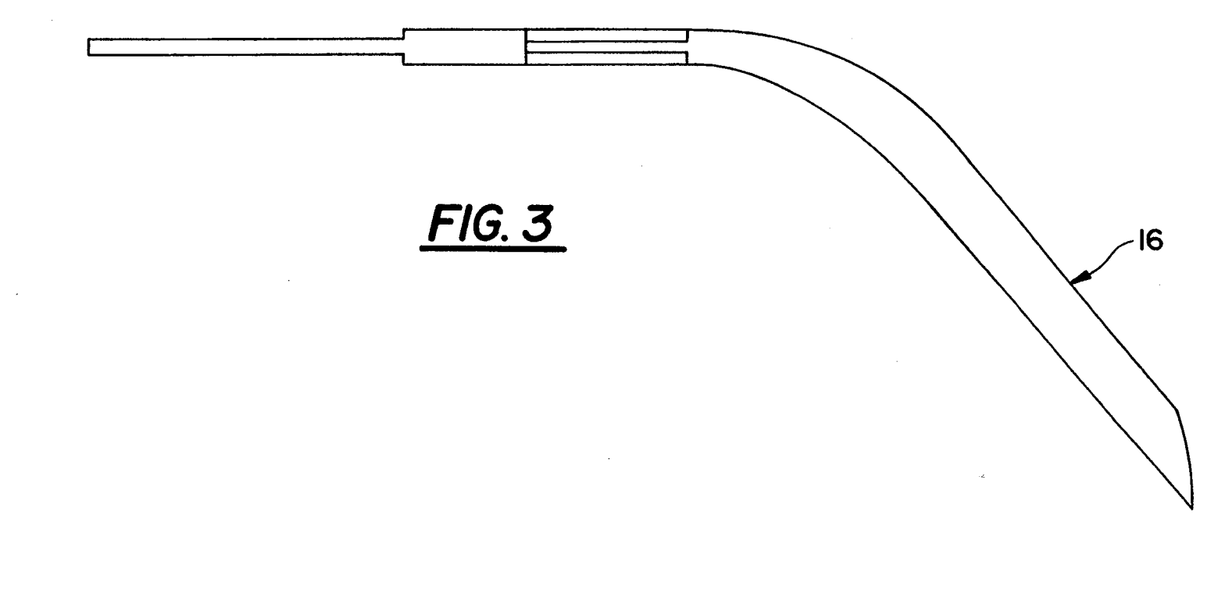
FIG. 3 is a plan view of the device of FIG. 1.
Figures 12, 13:
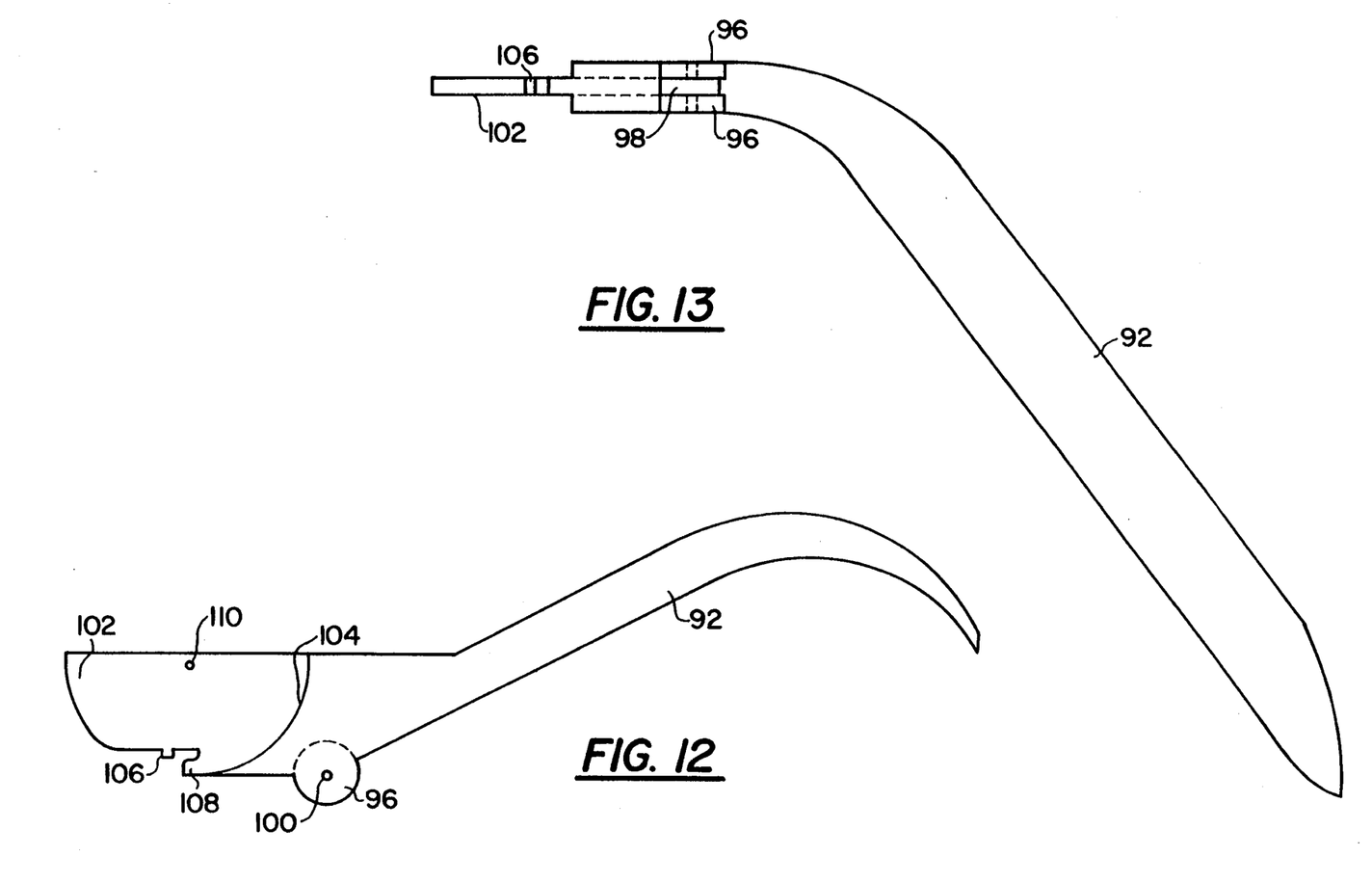
FIG. 12 is a front view of the upper handle member provided in accordance with the principles of the present invention.
FIG. 13 is a bottom view of the upper handle member of FIG. 12.

The intranasal stapling device 10 includes a handle assembly, generally indicated at 16, shown in FIGS. 1-3. The handle assembly includes an upper handle member 92 and lower handle member 94. The upper handle member 92 (FIGS. 12 and 13) has two protruding legs 96 defining a channel 98 therebetween. Each leg 96 has a bore 100 therethrough. A protruding portion 102 is defined at the distal end of the upper handle member. The protruding portion includes a curved portion 104 which mates with the curved portion 40 of the sliding arm member when assembled. The protruding portion is inserted into slot 42 of the stapler arm. The protruding portion 102 includes a bore 110 disposed therethrough. A pin 112 is disposed through bores 44 and 110 to pivotally couple the upper handle member to the stapler arm. The protruding portion further includes tabs 106 and 108. Tab 106 is sized to mate with recess 52 of the slide member 46, while tab 108 is sized to mate with notch 56 of the slide member, thus, operatively coupling the slide member 46 to the upper handle member, as shown in FIG. 1.

Figures 14, 15:
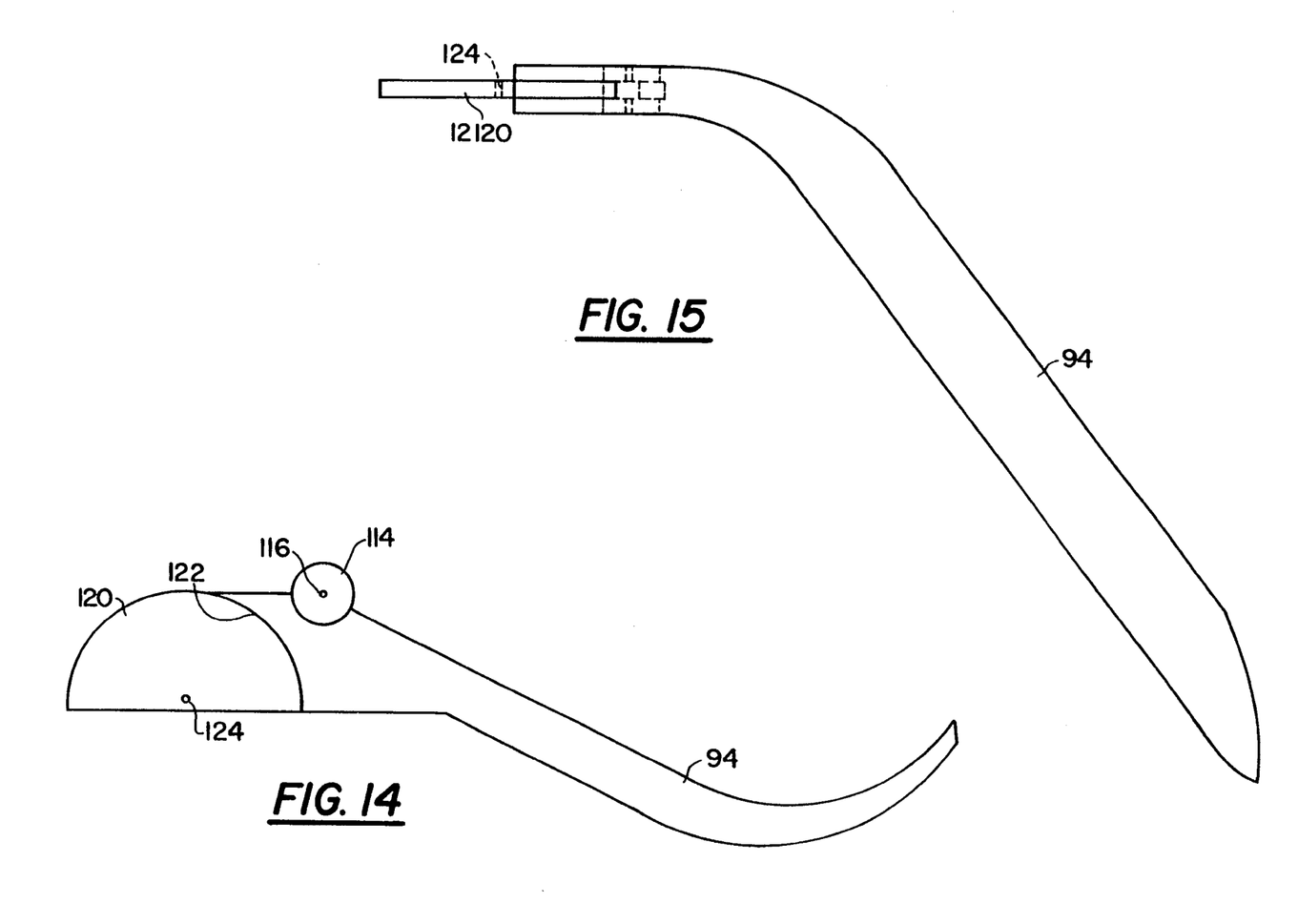
FIG. 14 is a front view of the lower handle member provided in accordance with the principles of the present invention.
FIG. 15 is a bottom view of the lower handle member of FIG. 14.

The lower handle member 94, as shown in FIGS. 14 and 15 includes a protruding leg member 114 which is sized to fit within channel 98 of the upper handle member when assembled. A bore 116 is defined through the leg member 114. A pin 118 is disposed through bore 116 and bore 100 of the upper handle member to pivotally couple the upper handle member to the lower handle member. The lower handle member further includes a projecting portion 120 having a curved portion 122. The curved portion is sized to mate with the curved portion 86 of the anvil arm when assembled. The projecting portion includes a bore 124 therethrough. A pin 126 is disposed through bore 114 and bore 90 of the anvil arm to pivotally couple the lower handle member to the anvil arm.

A spring 128 is disposed between the upper handle member and lower handle member and is affixed to each end thereof allowing the handle members to be resilient.

Figure 20:
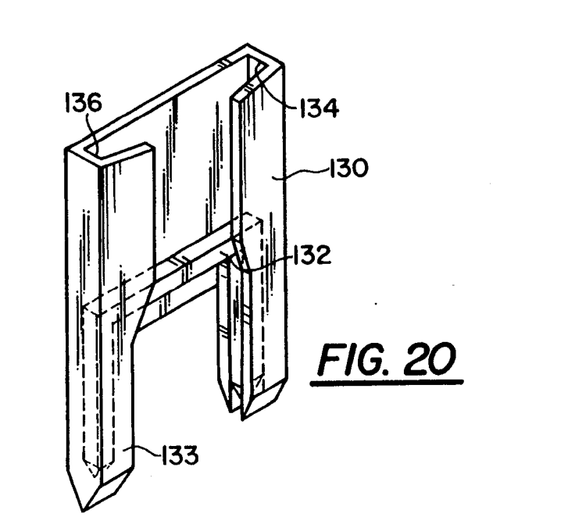
FIG. 20 is an enlarged perspective view of a staple capsule holding a staple, provided in accordance with the present invention.
Figure 21:
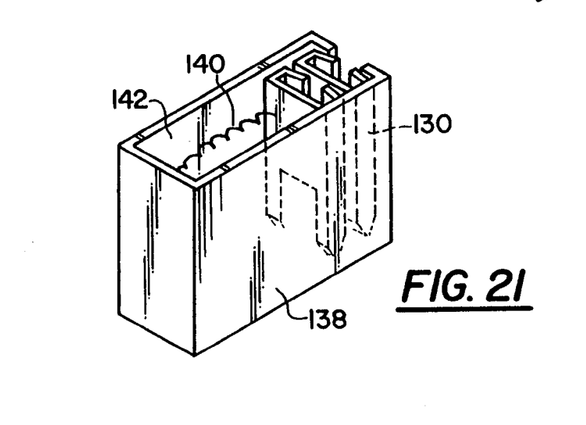
FIG. 21 is a perspective view of a magazine for holding staple capsules provided in accordance with the principles of the present invention.

The device 10 is further provided with staple capsules 130, one of which is shown in FIG. 20. Each capsule houses a staple 132. The staples are preferably made of bio-absorbable material and thus, need not be removed once inserted into the nasal tissue. Each capsule 130 includes interior surfaces 134, 136, which function as a guide rail for the staple for directing the staple out of the capsule, upon stapling. The capsule has both ends open with one open side wall. Leg members 133 are defined at the distal end of each capsule. The leg members have pointed ends enabling the capsule to function much like a trocar, enabling the capsule of pass easily along the nasal passage. The staple capsules are arranged in a row in a magazine 138 as shown in FIG. 21, and are biased against one side of the magazine by spring 140. The magazine 138 has an opening 142 in the top thereof to enable easy withdrawal of the capsule. The axial length of each capsule 130 is about 4 mm greater than the height of the staples to accommodate the stapler head.

Figure 4:
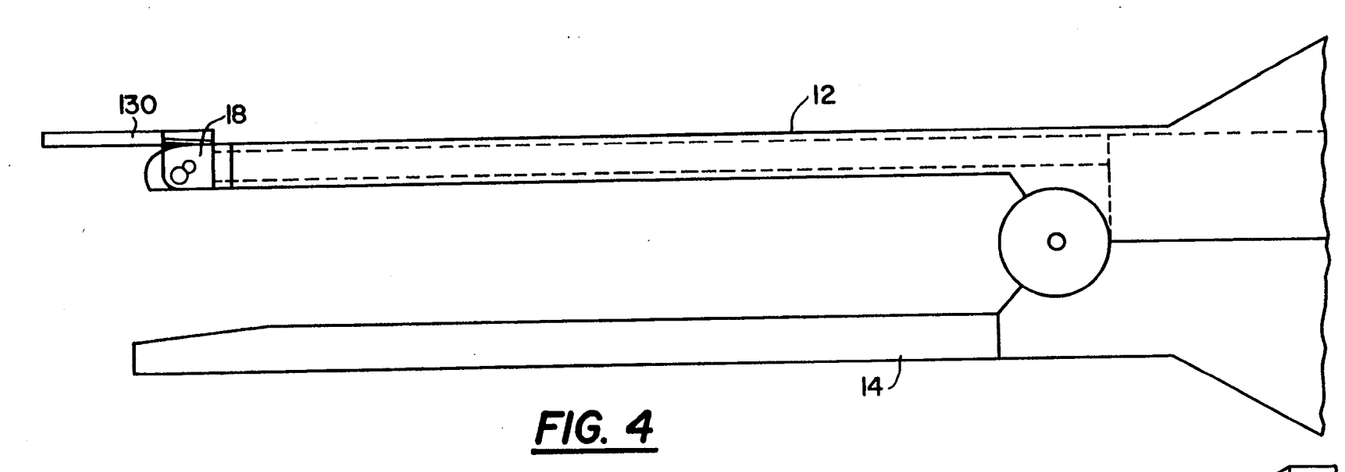
FIG. 4 is an enlarged front view of the distal portion of the device shown with the staple capsule in a relaxed state, prior to a stapling procedure.

With reference to the FIGURES, the operation of the intranasal stapling device 10 of the present invention can be appreciated. FIG. 1 shows the stapler device in a normally biased position. The stapler arm 12 and anvil arm 14 are initially in a parallel relation when the device 10 is in the normally biased position. While in the normally biased position, the stapler head 18 is in a low profile, inoperable position with the longitudinal axis of the capsule 130 and the longitudinal axis of the stapler arm 12 in a parallel relation (FIG. 4).

Figure 22:
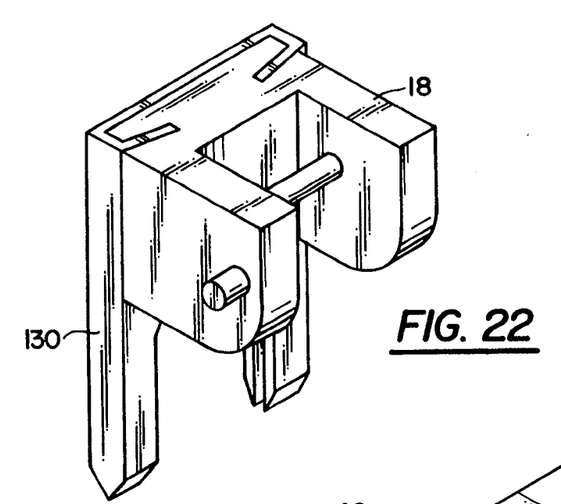
FIG. 22 is an enlarged perspective view of a staple capsule coupled to the stapler head.

The forwardmost staple capsule 130 in magazine 138 is removed therefrom and coupled to the stapler head 18 (FIG. 22). The head of the stapler head 18 engages with the groove of the capsule frictionally holding the capsule to the stapler head. The capsule housing the staple is then moved to the entrance of one nostril with the anvil arm being aligned with the other nostril.

The stapler arm 12 with the stapler head in the low profile position, and anvil arm 14 are introduced into the nose to the desired depth. The upper and lower handle members are then manually shifted slightly toward each other. As shown in FIG. 2, this slight actuation moves the distal portion of the anvil arm toward the distal portion of the stapler arm due to the device 10 pivoting about pins 85 and 118 causing pins 112 and 126 to move away from each other. This movement moves the slide member 46 forward. Thus, the slide member moves linearly within the stapler arm.

Figure 5:
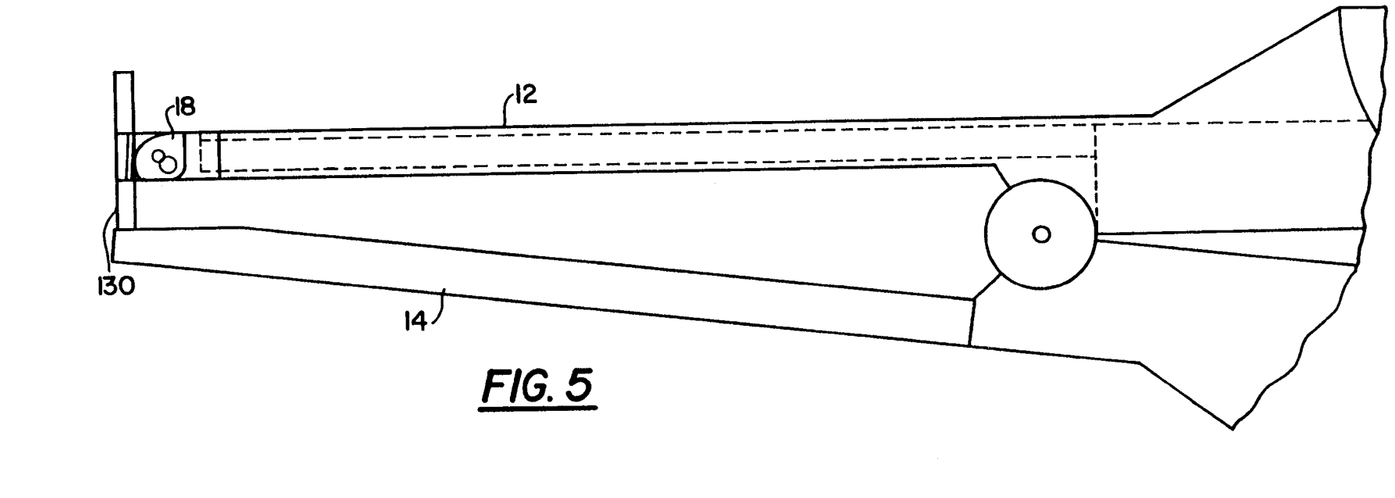
FIG. 5 is an enlarged view of the distal portion of the device shown in a biased state wherein the staple capsule is rotated for driving a staple.

Since the stapler head 18 is rotatably coupled to the slide member 46 by slot 48 and rod 62, the stapler head will rotate about protrusions 70 mating with the distal end of the stapler arm, moving the capsule to an operative position, perpendicular to the longitudinal axis of the stapler arm (FIG. 5). The rotation of the stapler head is preferably accomplished inside the nose and is possible because the septum is flexible after surgery. Once the stapler head is rotated to its operative position, so that the capsule is perpendicularly aligned with the anvil arm, the upper and lower handle members 92, 94, are brought closer together. The resilient transition portion 57 of the slide member permits further displacement of the handle inspite of the prior complete shifting of the head 18 and thus, prevents the stapler head 18 from locking and binding (FIG. 2). This second action of the handle members brings the staple capsule 130 and anvil arm 12 toward one another. Because further motion of the capsule is restricted by the septal tissue, further actuation of the handle causes the stapler head to force the staple out of the capsule and through the nasal tissue. In the event the staple extends all the way through the septum, the staple will be bent against the anvil. The stapler head moves down into the capsule, taking the previous position of the staple. The handle members are then released, which permits the slide member 46 to return its original, pre-stapling position which in turn shifts the capsule and stapler head to rotate back to the low profile position and be withdrawn. The capsule remains on the stapler head until it is manually removed.

It can be appreciated that the intranasal stapling device 10 of the present invention permits relatively large bio-absorbable staples to be delivered through a small entrance (the nares), down a narrow passageway to the eventual destination deep within the nose. For increased accuracy, a nasal speculum may be employed which allows direct visualization of the stapling procedure. If cartilage is to be replaced, pockets for insertion of the cartilage can be created by stapling. In addition, tears in the mucosa can be repaired with staples, and soft tissue grafts for perforation can be accurately anchored with stapling.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims. For example, although a method and device for intranasal septal stapling has been described, the device of the invention could be used for stapling other structures during other surgical procedures as well.

What is claimed is:

1. A stapling device comprising:
   first and second arms, each of said arms having a distal portion and a proximal portion;
   a stapler head rotatably coupled to a free end of said distal portion of said second arm, said stapler head having a first, inoperative position and a second, operative position;
   means for moving said stapler head from said inoperative position to said operative position;
   means for pivotally coupling said first arm to said second arm; and
   first and second handle members each pivotally coupled to said proximal portions of said first and second arms, said moving means being cooperable with at least one of said handle members so that after displacement of said moving means by initial movement of said handle members to place said stapler head in said operative position, further displacement of said handle members moves said second arm to bring said stapler head and said first arm into contact with tissue structure to be stapled.

2. A stapling device as claimed in claim 1, wherein said moving means is an elongated member slidingly disposed within a channel of said second arm, said elongated member having proximal and distal ends, said distal end being coupled to said stapler head, said proximal end being coupled to at least one of said handle members.

3. A stapling device as claimed in claim 2, wherein said elongated member includes a resilient portion permitting movement of the elongated member without binding said stapler head.

4. A stapling device as claimed in claim 1, in combination with a capsule having first and second ends and at lease one staple disposed between said ends, said capsule including guide surfaces for guiding the staple out of the capsule, said capsule being open at each said first and second end and having a staple holding channel defined therethrough, said stapler head including a staple driving portion sized for insertion in and frictional engagement with said channel, said stapler head being inserted into one of said open ends of said capsule and being frictionally held thereto, said stapler head being constructed and arranged to move through said capsule upon said further displacement of said handle members.

5. A stapling device as claimed in claim 4, wherein said staple is formed from bio-absorbable material.

6. A stapling device as claimed in claim 4, in combination with means for storing a plurality of said capsules, said capsules placed adjacent to each other in said storing means, said storing means including an access opening, said capsules being biased toward said access opening for removal therefrom.

7. A stapling device as claimed in claim 1, wherein said distal portion of each of said arms extends to said proximal portion of each of said arms, said proximal portions of said arms being of greater height and width than said distal portions.

8. A stapling device as claimed in claim 1, wherein said distal portion of said second arm includes a channel defined along a longitudinal length thereof, said moving means comprising an elongate arm element slidably disposed within said channel, a distal end of said arm element being pivotably coupled to said stapler head.

9. A stapling device as claimed in claim 8, wherein said distal end of said arm element includes first and second leg members defining a space therebetween, each said leg member having a bore therethrough, said stapler head having projections extending from opposing surfaces thereof, said stapler head being disposed between said leg members in said space, with said projections being disposed in said bores.

10. A stapling device as claimed in claim 8, said handle members are pivotably coupled to each other and said arm element is coupled to one of said handle members so that said initial movement of said handle members moves said arm element thereby enabling said stapler head to pivot from said inoperative position to said operative position.

11. A stapling device as claimed in claim 1, wherein said handle members are normally biased away from each other.

12. A stapling device as claimed in claim 1, wherein said first arm includes anvil means for engaging and deflecting legs of a staple urged thereagainst.

13. A stapling device as claimed in claim 1, wherein each of said distal ends of said arms and said stapler head are constructed and arranged to be insertable into and operable within a nasal passage.

* * * * *